United States Patent [19]

Rodriguez et al.

[11] 4,139,628

[45] Feb. 13, 1979

[54] AMINO-SPIRO[OXA(OR THIA)CYCLOALKANE-PENAM]-CARBOXYLIC ACID DERIVATIVES

[75] Inventors: Ludovic Rodriguez, Brussels; Jacques Leclercq, Braine l'Alleud; Pierre Ykman; Eric Cossement, both of Brussels, all of Belgium

[73] Assignee: U C B, Societe Anonyme, Belgium

[21] Appl. No.: 869,860

[22] Filed: Jan. 16, 1978

[30] Foreign Application Priority Data

Jan. 18, 1977 [GB] United Kingdom ............... 1906/77

[51] Int. Cl.² ................... A61K 31/43; C07D 499/44
[52] U.S. Cl. ............................. 424/271; 260/239.1; 260/306.7 C
[58] Field of Search ............... 424/271; 260/306.7 C, 260/239.1

[56] References Cited

U.S. PATENT DOCUMENTS 2,951,839  9/1960  Doyle et al. ............... 260/239.1

Primary Examiner—Nicholas S. Rizzo
Attorney, Agent, or Firm—Wenderoth, Lind & Ponack

[57] ABSTRACT

Amino-spiro[oxa(or thia)cycloalkane-penam]-carboxylic acid derivatives having the formula

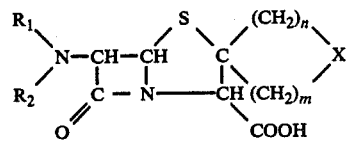

wherein X is a sulfur or oxygen atom or the sulfinyl group, n is 1 or 2, m is 1 or 2, $R_1$ is hydrogen, $R_2$ is one of the radicals known in the chemistry of the penicillins, preferably 2-phenylacetyl, 2-amino-2-phenylacetyl, 5-methyl-3-phenyl-4-isoxazolecarbonyl or 2,6-dimethoxybenzoyl, or $R_1$ and $R_2$ together represent a bivalent radical $R_3$, preferably (hexahydro-1H-azepin-1-yl)methylene and their therapeutically acceptable non-toxic salts and process for preparing the same.

These compounds have valuable antibacterial properties and are useful as therapeutic agents in the treatment of infectious diseases caused by Gram-positive and Gram-negative bacteria.

13 Claims, No Drawings

AMINO-SPIRO[OXA(OR THIA)CYCLOALKANE-PENAM]-CARBOXYLIC ACID DERIVATIVES

The present invention relates to new anti-bacterially active amino-spiro[oxa(or thia)cycloalkane-penam]-carboxylic acid derivatives and to processes for preparing the same.

More particularly, the present invention relates to amino-spiro[oxa(or thia)cycloalkane-penam]-carboxylic acid derivatives of the general formula:

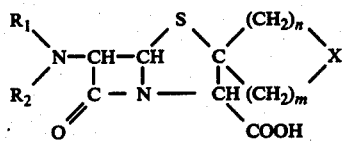

wherein X is a sulfur or oxygen atom or the sulfinyl group, n and m, which can be the same or different, are 1 or 2, preferably 2, $R_1$ is a hydrogen atom and $R_2$ is a radical selected from those known in the chemistry of the penicillins, preferably a 2-phenylacetyl, 2-amino-2-phenylacetyl, 5-methyl-3-phenyl-4-isoxazolecarbonyl or 2,6-dimethoxybenzoyl radical, or $R_1$ and $R_2$ together represent a bivalent radical $R_3$, preferably the (hexahydro-1H-azepin-1-yl)methylene radical; as well as the pharmaceutically-acceptable non-toxic salts thereof, preferably the sodium and potassium salts.

The penicillins are a group of compounds having the following general formula:

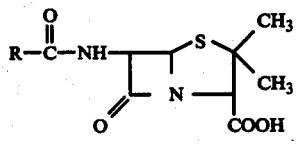

wherein R may represent one of a multitude of substituents, those most currently used being mentioned in Ullmann's Encyklopadie der Technischen Chemie, 4th Edition, 7, (1974), 651-652.

Most of the investigations hitherto carried out in this field were based on the search for new substituents R, while the basic ring system of the molecule remained unchanged. Nevertheless, a number of attempts have been made to study the influence of some variations in the ring system on the activity of the compounds thus obtained. Thus, compounds analogous to penicillins have been proposed but in which the gem-dimethyl group situated in the alpha-position with regard to the sulfur atom was replaced by other groups. The following groups have been proposed:

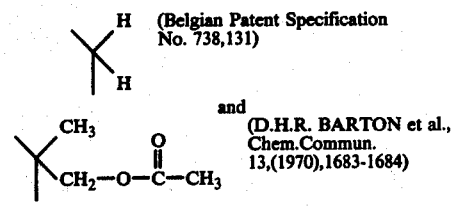

However, it was concluded at the time of these different attempts, that the nature of the substituents on the carbon atom in the alpha-position with regard to the sulfur atom was not essential for the antibacterial activity of the penicillins (see, for example, R. J. STOODLEY, Progress in Organic Chemistry, 8, (1973), 106. More recently, the following groups have also been proposed:

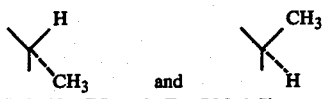

(P.J. CLAES et al., Eur.J.Med.Chem. Chimica Therapeutica,10,(1975),573-577)

The conclusion with regard to antibacterial activity was the same.

We have now found that, by suitably substituting the carbon atom on the alpha-position with regard to the sulfur atom, it is possible to obtain compounds, the antibacterial activities of which are at least equal to those of the corresponding penicillins. Furthermore, these new compounds are particularly interesting in the treatment of infections caused by Gram-negative bacteria which produce beta-lactamases. These new compounds and the preparation and use thereof form the subject matter of the present invention.

The nomenclature used hereinafter is that proposed by R. J. STOODLEY, loc. cit. 102-103. In particular, the following ring system is designated "penam":

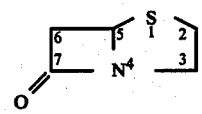

The new compounds of the present invention are amino-spiro[oxa(or thia)cycloalkane-penam]-carboxylic acids in which the amino group is substituted by a substituent known in the chemistry of penicillins.

These compounds are analogous to penicillins, wherein the carbon atom in the 2-position of the "penam" ring is substituted by an oxa- or thia-alkylene chain, which forms with this carbon atom a heterocycle. Thus, these compounds have the structure of a spiro heterocycle, constituted by the penam ring and by a saturated monocyclic heterocycle having an oxygen or sulfur atom. In addition, this sulfur atom may carry an oxygen atom.

Among the substituents known in the chemistry of penicillins, mention is made, in particular, of those mentioned in Ullmann's Encyklopädie der Technischen Chemie, loc.cit.

Thus, when substituent $R_2$ is a 2-phenylacetyl radical, the compounds of the present invention are similar to benzylpenicillin (penicillin G); when $R_2$ is a 2-amino-2-phenylacetyl radical, the compounds of the present invention are similar to ampicillin; when $R_2$ is a 5-methyl-3-phenyl-4-isoxazolecarbonyl radical, the compounds of the present invention are similar to oxacillin and when $R_2$ is a 2,6-dimethoxybenzoyl radical, the compounds of the present invention are similar to methicillin.

When $R_1$ and $R_2$ together represent a (hexahydro-1H-azepin-1-yl)methylene radical, the compounds of the present invention are similar to the penicillins which form the subject matter of British Pat. Specification No. 1,293,590. Therefore, in this case, the compounds have side chains connected to the penam ring system by a

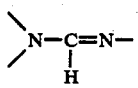

group and these compounds are referred to as "amidinopenicillins". This type of side chain has been introduced recently into the chemistry of penicillins and it leads to compounds the activity of which at the bacterial wall is due to a mechanism which is different from that of the penicillins having traditional side chains, such as those defined above. The difference in their mode of action on the bacteria imparts a novel antibacterial spectrum to the amidinopenicillins.

As regards stereochemistry, the existence of three asymmetric carbon atoms at $C_3$, $C_5$ and $C_6$ should lead to the formation of 8 isomers which can be grouped into 4 racemic diastereoisomers. The kinetics of the reactions leads, in fact, to the formation of only three alpha-, beta- and gamma-racemates. The alpha-racemate, the relative configuration of which correspond to that of natural penicillin, i.e. the configuration S at $C_3$ and the configuration R at $C_5$ and $C_6$, is preferably isolated from this mixture.

The compounds of general formula (I) according to the present invention, in which X is a sulfur or oxygen atom, n is 1 or 2, m is 1 or 2, $R_1$ is a hydrogen atom and $R_2$ is radical selected from those known in the chemistry of penicillins, preferably a 2-phenylacetyl, 2-amino-2-phenylacetyl, 5-methyl-3-phenyl-4-isoxazolecarbonyl or 2,6-dimethoxybenzoyl radical, are obtained by subjecting an amino-spiro[oxa(or thia)cycloalkane-penam]-carboxylic acid or an ester or salt thereof, to an acylation reaction.

Thus, the present invention also provides a process for the preparation of an amino-spiro[oxa(or thia)cycloalkane-penam]-carboxylic acid derivative of the general formula (I):

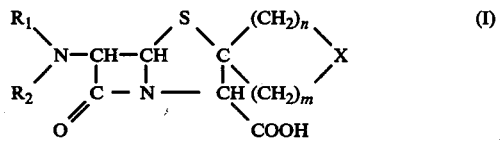

wherein X is a sulfur or oxygen atom, n is 1 or 2, m is 1 or 2, $R_1$ is a hydrogen atom and $R_2$ is a radical selected from those known in the chemistry of penicillins, which comprises reacting an amino-spiro[oxa(or thia)cycloalkanepenam]-carboxylic acid of the formula (II):

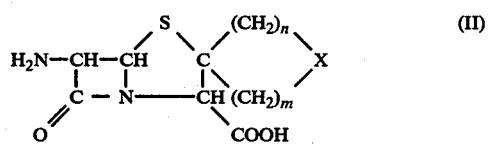

in which n, m and X have the meanings given above, or an ester or salt thereof, with a halide of a monocarboxylic acid of the formula $R_2OH$ or with a functional equivalent thereof, $R_2$ having the meaning given above, this acid halide preferably being phenylacetyl chloride, 2-phenylglycyl chloride, 5-methyl-3-phenyl-4-isoxazolecarbonyl chloride or 2,6-dimethoxybenzoyl chloride.

The functional equivalents of the above-mentioned acid halides used as acylating agents for the primary amino radical of the amino-spiro[oxa(or thia)cycloalkane-penam]-carboxylic acids of the formula (II) are, in particular, the acid anhydrides, including the mixed anhydrides and especially the mixed anhydrides formed with stronger acids, such as the lower aliphatic monoesters of carbonic acid, alkylsulfonic and arylsulfonic acids and the acids which have a more pronounced hindrance, such as diphenylacetic acid. Furthermore, an acid azide or an active ester or thioester (for example with p-nitrophenol, 2,4-dinitrophenol, thiophenol or thioacetic acid) may be use but, as a variant, the free acid itself may be condensed with the amino-spiro[oxa(or thia)cycloalkane-penam]-carboxylic acids of formula (II), after the free acid has first been activated by reacting it, for example, with (chloromethylene)dimethylammonium chloride (see British Pat. Specification No. 1,008,170 and NOVAK and WEICHET, Experientia, XXI, 6, (1965), 360) or by means of enzymes, or with an N,N'-carbonyldiimidazole or an N,N'-carbonylditriazole (see British Pat. Specification No. 967,108), or with a carbodiimide, for example N,N'-dicyclohexylcarbodiimide (see Example II.1.a) and b)), N,N'-diisopropylcarbodiimide or N-cyclohexyl-N'-(2-morpholinoethyl)-carbodiimide (see SHEEHAN and HESS, J.Am.Chem.Soc. 77, (1955), 1067) or an alkynylamine (see BUIJLE and VIEHE, Angew.Chem..International Edition, 3, (1964), 582) or a keteneimine (see STEVENS and MUNK, J.Am.Chem.Soc. 80, (1958), 4065) or an isoxazolium salt (see WOODWARD et al., J.Am.Chem.Soc. 83, (1961), 1010). It is also possible to use the corresponding azolides instead of the acid halides.

When the starting compound used is an ester of the amino-spiro[oxa(or thia)cycloalkane-penam]-carboxylic acid of the formula (II), preferably the benzyl ester, the process according to the present invention includes a second stage which comprises a hydrogenolysis of the resulting esters to the corresponding acids. These esters have a weak antibacterial activity and are essentially useful as intermediates in the synthesis of the corresponding acids or salts.

The starting compounds may be, as desired, the amino-spiro[oxa(or thia)cycloalkane-penam]-carboxylic acids of the formula (II) or the salts or esters thereof. Nevertheless, it has been found that it is preferable, with regard to yield, to use, in certain cases, the esters and, in other cases, the acids themselves. In particular, when the substituent $R_2$ is a 2-phenylacetyl, 2-amino-2-phenylacetyl or 2,6-dimethoxybenzoyl radical, it is preferable to start from an ester, for example a benzyl ester, of the corresponding amino-spiro[oxa(or thia)cycloalkane-penam]-carboxylic acid, and to subject the resulting compound to a subsequent debenzylation reaction to give the free acid. When, on the other hand, the substituent $R_2$ is a 5-methyl-3-phenyl-4-isoxazolecarbonyl radical, it is preferable to start from the acid itself. Nevertheless, it must be remembered that the amino-spiro[oxa(or thia)cycloalkanepenam]-carboxylic acids are themselves always obtained from the corresponding esters, because it is necessary temporarily to protect the acid function. In other words, the stage of conversion from ester into acid is not a supplementary stage because it is, in fact, simply displaced in the general synthesis process: in certain cases it is carried out prior to the acylation reaction and in certain cases it is carried out after this acylation reaction.

The amino-spiro[oxa(or thia)cycloalkane-penam]-carboxylic acids of the formula II and the alkali metal salts and esters thereof which are the starting materials for the preparation of the compounds according to the present invention, as well as the preparation thereof form the subject matter of our Application Ser. No. 869,859 filed concurrently herewith, to which reference is made for a detailed description.

The starting compounds of the formula (II) can be prepared as follows:

(1) reacting tert-butyl 2-formyl-2-phthalimido-acetate of formula (III) with an alpha-amino-mercapto-oxa(or thia)cycloalkaneacetic acid of the formula (IV) to give the alpha isomer of a tert-butyl alpha-phthalimido-dithia(or oxa-thia)-azaspiroalkane acetate of formula (V) in accordance with the equation:

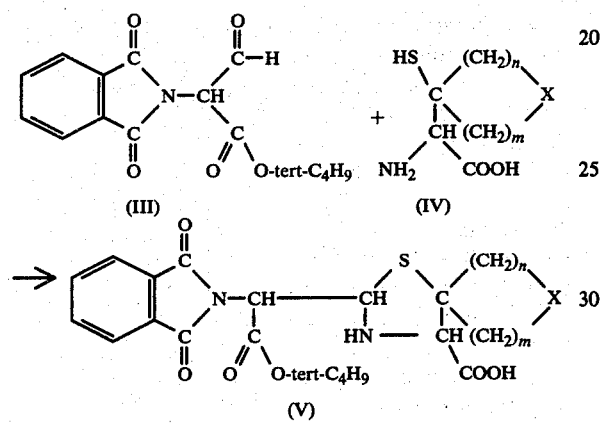

(2) preparing the benzyl ester of formula (VI) by reaction with a benzyl halide in accordance with the equation:

(V) + Bz—Hal →

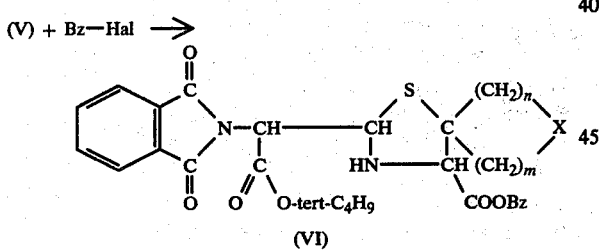

(3) subjecting the benzyl ester of formula (VI) to a hydrazinolysis to give a tert-butyl alpha-amino-dithia(or oxa-thia)-azaspiroalkaneacetate hydrochloride of the formula (VII) in accordance with the equation:

(VI) + $H_2N-NH_2$ →

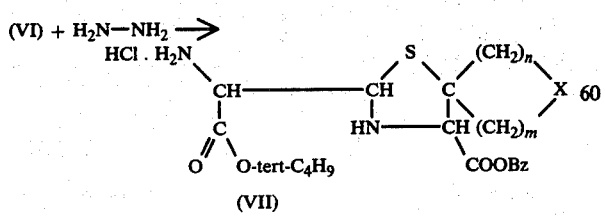

(4) subjecting the compound of formula (VII) to a partial acid hydrolysis to give the corresponding alpha-amino-dithia(or oxa-thia)-azaspiroalkane-acetic acid hydrochloride of the formula (VIII) in accordance with the equation:

(VII) $\xrightarrow{H^+}$

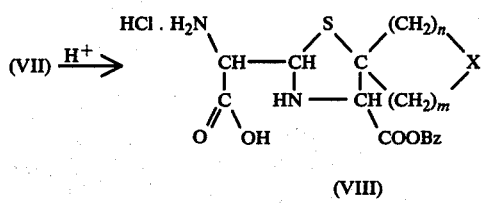

(5) reacting the compound of formula (VIII) with trityl chloride to give an alpha-tritylamino-dithia(or oxa-thia)-azaspiroalkaneacetic acid of formula (IX) in accordance with the equation:

(VIII) + $(C_6H_5)_3 \equiv C-Cl$ →

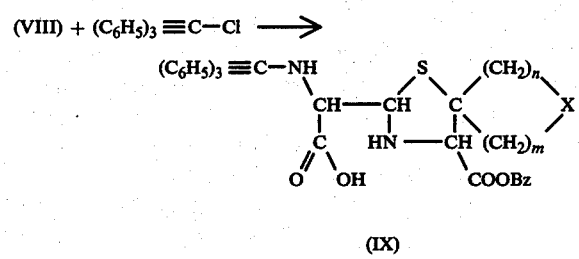

(6) cyclizing the compound of formula (IX) with a carbodiimide (CI) to give a benzyl tritylamino-spiro[oxa(or thia)cycloalkane-penam]-carboxylate of the formula (X), in accordance with the equation:

(IX) $\xrightarrow{CI}$

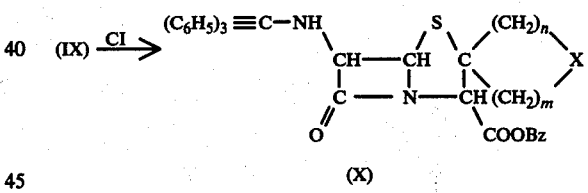

(7) treating (X) with p-toluenesulfonic acid to give the corresponding benzyl amino-spiro[oxa(or thia)-cycloalkane-penam]-carboxylate p-toluenesulfonate of the formula (XI), in accordance with the equation:

(X) $\xrightarrow{\text{p-toluenesulfonic acid}}$

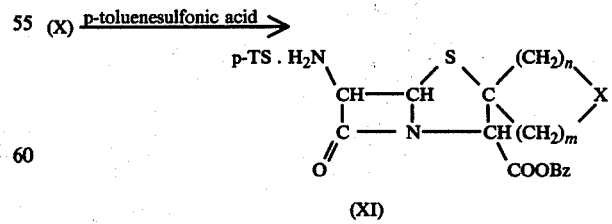

(8) finally subjecting the compound of formula (XI) to a hydrogenolysis to give an amino-spiro[oxa(or thia)cycloalkane-penam]-carboxylic acid of the formula (II), in accordance with the equation:

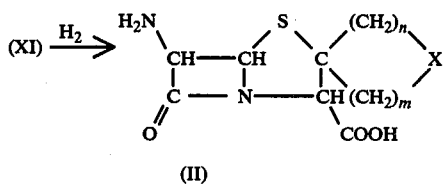

(II)

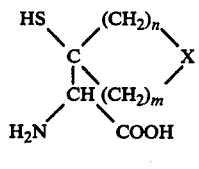

(IV)

In the above formulae, Bz is a benzyl radical, p-TS represents p-toluenesulfonic acid, Hal is a halogen atom, for example a bromine atom, X is an oxygen or sulfur atom and n and m, which can be the same or different, are 1 or 2.

The preparation of tert-butyl 2-formyl-2-phthalimido-acetate of formula (III) is described in the literature (see SHEEHAN et al., J.Am.Chem.Soc. 76, (1954), 158–60).

The starting compounds of the formula (IV) can be prepared, for example, by the following process:

(1) condensing an R' 2-isocyanoacetate of the formula (XII) with an oxa(or thia)cycloalkanone of the formula (XIII) using a suspension of sodium hydride in tetrahydrofuran (THF), to give an R' alpha-formamido-oxa(or thia)cycloalkane-$\Delta^\alpha$-acetate of the formula (XIV) in accordance with the equation:

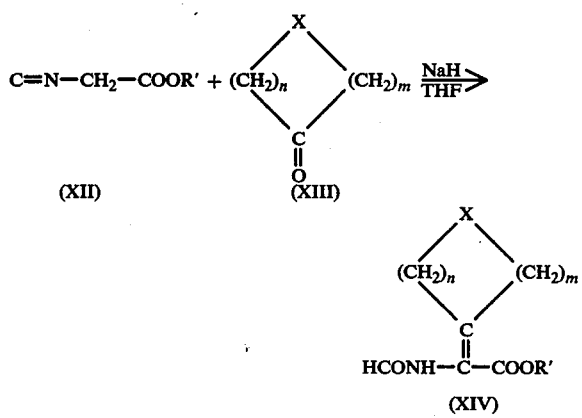

(2) cyclizing the compound of formula (XIV) by treatment with phosphorus pentasulfide to give an R' dithia(or oxa-thia)-azaspiroalkenecarboxylate of the formula (XV) in accordance with the equation:

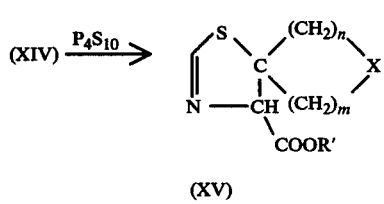

(3) subjecting the compound of formula (XV) to hydrolysis, which is accompanied by decyclization, to give an alpha-amino-mercapto-oxa(or thia)cycloalkaneacetic acid of the formula (IV), in accordance with the equation:

In these formulae, R' is an alkyl radical containing 1 to 3 carbon atoms or a benzyl radical, X is an oxygen or sulfur atom and n and m, which can be the same or different, are 1 or 2.

It is clear that the two enantiomeric forms of the compounds of the formula (IV) can be separated, which leads directly to the desired diastereoisomer (V) in a pure form.

By "pharmaceutically acceptable non-toxic salts" are to be understood, in particular, the metal salts, such as sodium, potassium, calcium and aluminium salts, the ammonium salts and the salts of amines, such as the trialkylamines, particularly triethylamine, procaine, dibenzylamine, N-benzyl-beta-phenethylamine, L-ephenamine, N,N'-dibenzyl-ethylenediamine, dehydroabietylamine, N,N'-bis-dehydroabietyl-ethylenediamine and N-(lower alkyl)-piperidines, such as N-ethyl-piperidine, and, generally speaking, the salts already known for penicillins G and V (see Ullmann's Encyklopädie, loc.cit. p. 653). These salts can be prepared from the corresponding acids by known methods.

In the particular case in which $R_2$ is a 2-amino-2-phenylacetyl radical, the products of the present invention can be converted into their acid addition salts, for example with pharmaceutically acceptable non-toxic acids, such as acetic acid, citric acid, succinic acid, ascorbic acid, hydrochloric acid, hydrobromic acid, sulfuric acid or phosphoric acid.

The compounds of general formula (I) in which X is a sulfur or oxygen atom, n is 1 or 2, m is 1 or 2 and $R_1$ and $R_2$ together represent a bivalent radical $R_3$, preferably the (hexahydro-1H-azepin-1-yl)methylene radical, can be prepared by reacting an amino-spiro[oxa(or thia)cycloalkane-penam]-carboxylic acid of formula (II) or an ester or salt thereof with an activated derivative of a compound of the formula $R_3=O$ and preferably with an activated derivative of hexahydro-1H-azepin-1-carboxaldehyde.

The activated derivative of the compound $R_3=O$ can be, for example and preferably the chloride of the corresponding amide obtained by reaction with oxalyl chloride or a complex obtained by reaction with dimethyl sulfate. Preferably, there are used the following compounds, which are activated derivatives of hexahydro-1H-azepin-1-carboxaldehyde:

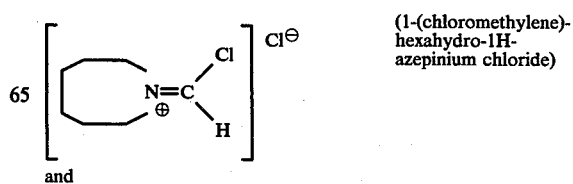

(1-(chloromethylene)-hexahydro-1H-azepinium chloride)

and

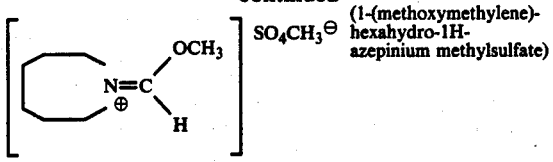

$$\left[\begin{array}{c}\text{(structure)}\\ N=C\overset{OCH_3}{\underset{H}{\oplus}}\end{array}\right] SO_4CH_3^{\ominus} \quad \begin{array}{l}\text{(1-(methoxymethylene)-}\\ \text{hexahydro-1H-}\\ \text{azepinium methylsulfate)}\end{array}$$

The compounds of general formula (I), in which X is the sulfinyl group (S→O) and n, m, $R_1$ and $R_2$ have the meanings already mentioned above, are obtained by subjecting an amino-spiro[oxa(or thia)cycloalkane-penam]-carboxylic acid derivative of formula (I), wherein X is a sulfur atom, or an ester or a salt thereof, to an oxidation by means of an organic peracid, such as peracetic, perbenzoic or preferably m-chloroperbenzoic acid. When the starting compound used is an ester of a derivative of formula (I), for example the benzyl ester, the ester obtained should, of course, subsequently be converted into the corresponding acid by hydrogenolysis.

The present invention relates also to the use of the compounds of general formula (I), as well as of their pharmaceutically acceptable non-toxic salts, as antibacterial agents, as dietetic supplements for animal foodstuffs and as therapeutic agents for man and animals in the treatment of infectious diseases caused by Gram-positive and Gram-negative bacteria.

The compounds of the present invention possess a very broad spectrum of antibacterial activity, both against Gram-positive and against Gram-negative bacteria but they are particularly interesting for combating Gram-negative strains which produce beta-lactamases.

The following Examples are given for the purpose of illustrating the present invention:

EXAMPLE I. Preparation of (2″-phenylacetamido)-spiro[oxa(or thia)cycloalkane-penam]-carboxylic acids and their derivatives I.1. Preparation of benzyl (2″-phenylacetamido)-sprio[oxa(or thia)cycloalkane-penam]-carboxylate (a) Benzyl 6-(2″-phenylacetamido)-2′,3′,5′,6′-tetrahydro-spiro[penam-2,4′-[4H]-pyran]-3-carboxylate 303 mg (0.003 mole) of triethylamine in 10 ml of anhydrous dichloromethane are added all at at once at ambient temperature and with stirring to a suspension of 1.56 g (0.003 mole) of benzyl 6-amino-2′,3′,5′,6′-tetrahydrospiro[penam-2,4′-[4H]pyran]-3-carboxylate p-toluenesulfonate (prepared according to the method described in Example V.1 of our Application Ser. No. 869,859 filed concurrently herewith) in 100 ml of anhydrous dichloromethane. The p-toluenesulfonate dissolves instantaneously. The reaction mixture is cooled to between 0° and −5° C. and then there are added alternately and in small portions, over a space of about 1 hour, 510 mg (0.0033 mole) of phenylacetyl chloride in 10 ml of dichloromethane and 335 mg (0.0033 mole) of triethylamine in 10 ml of dichloromethane. Stirring is continued for 2 hours, whilst the reaction mixture gradually returns to ambient temperature.

After washing the organic phase successively with 1/20 N hydrochloric acid, 5% aqueous sodium hydrogen carbonate solution and water and then drying over anhydrous sodium sulfate, it is evaporated to dryness. The residue obtained is recrystallized either from ethyl acetate or from a diethyl ether/hexane mixture (1:3) to give 1.32 g (yield 94.4% of theory) of benzyl 6-(2″-phenylacetamido)-2′,3′,5′,6′-tetrahydro-spiro[penam-2,4′-[4H]pyran]-3-carboxylate; M.P. 130° C.

Analysis for $C_{25}H_{26}N_2O_5S$ (M.W. = 466) (as %)

|  | C | H | N |
|---|---|---|---|
| calculated : | 64.37 | 5.58 | 6.00 |
| found : | 64.70 | 5.81 | 6.30 |

Infra-red spectrum (KBr) in cm$^{-1}$:

| | |
|---|---|
| 3240 | NH |
| 3040 } | |
| 2940 } | CH and $CH_2$ |
| 2830 | |
| 1772 | CO beta-lactam |
| 1743 | CO ester |
| 1635 | CO amide |
| 725 } | monosubstituted phenyl |
| 688 } | |

N.M.R. ($CDCl_3$-tetramethylsilane (TMS)):

| ppm | multiplicity | integration | attribution |
|---|---|---|---|
| 1 to 2.10 | m | 4 H | two $H_{2'}$ and two $H_{6'}$ |
| 3 to 4.10 | m | 4 H | two $H_{3'}$ and two $H_{5'}$ |
| 3.64 | s | 2 H | $CH_2$ of phenylacetyl group |
| 4.53 | s | 1 H | $H_3$ |
| 5.17 | s | 2 H | $CH_2$ of benzyl group |
| 5.57 | q (J=4 cps) | 2 H | $H_5$ and $H_6$ |
| 6 | m | 1 H | NH |
| 7.35 | s | 10 H | two phenyl groups |

(m = multiplet, s = singlet, q = quartet).

(b) Benzyl 6-(2″-phenylacetamido)-2′,3′,5′,6′-tetrahydro-spiro[penam-2,4′-[4H]thiopyran]-3-carboxylate This compound is prepared in the same manner as the preceding one, but starting with benzyl 6-amino-2′,3′,5′,6′-tetrahydro-spiro[penam-2,4′-[4H]thiopyran]-3-carboxylate p-toluenesulfonate (prepared according to the method described in Example V.2 of our Application Ser. No. 869,859 filed concurrently herewith). After recrystallization of the obtained compound from diethyl ether, the yield is 56% of theory. M.P. 138°–141° C.

Analysis for $C_{25}H_{26}N_2O_4S_2$ (M.W. = 482) (as %)

|  | C | H | N |
|---|---|---|---|
| calculated : | 62.20 | 5.40 | 5.81 |
| found : | 62.01 | 5.45 | 5.80 |

Infra-red spectrum (KBr) in cm$^{-1}$:

| | |
|---|---|
| 3260 | NH |
| 3035 } | |
| 2900 } | CH and $CH_2$ |
| 1785 | CO beta-lactam |
| 1760 | CO ester |
| 1650 | CO amide |
| 1530 | NH amide |
| 730 } | monosubstituted phenyl |
| 695 } | |

N.M.R. ($CDCl_3$-TMS):

| ppm | multiplicity | integration | attribution |
|---|---|---|---|
| 1.5 to 3 | m | 8 H | twice: $H_{2'}$, $H_{3'}$, $H_{5'}$ and $H_{6'}$ |
| 3.65 | s | 2 H | $CH_2$ of phenylacetyl group |
| 4.48 | s | 1 H | $H_3$ |
| 5.2 | s | 2 H | $CH_2$ of benzyl group |
| 5.2 to 5.8 | m | 2 H | $H_5$ and $H_6$ |
| 5.9 to 6.7 | m | 1 H | NH |
| 7 to 7.7 | m | 10 H | two phenyl groups |

(c) The following compounds are prepared in the same manner:

benzyl 6′-(2″-phenylacetamido)-4,5-dihydro-spiro[furan-3(2H),2′-penam]-3′-carboxylate, benzyl 6-(2″-phenylacetamido)-4′,5′-dihydro-spiro[penam-2,3′(2′H)-thiophene]-3-carboxylate, benzyl 6′-(2″-phenylacetamido)-spiro[oxetane-3,2′-penam]-3′-carboxylate, benzyl 6-(2''-phenylacetamido)-spiro[penam-2,3'-thietane]-3-carboxylate.

(d) Benzyl 6-(2''-phenylacetamido)-2',3',5',6'-tetrahydro-spiro[penam-2,4'-[4H]-thiopyran]-3-carboxylate 1'-oxide 1.6 g (0.0033 mole) of benzyl 6-(2''-phenylacetamido)-2',3',5',6'-tetrahydrospiro[penam-2,4'-[4H]thiopyran]-3-carboxylate (prepared as indicated in 1(b) hereinbefore) are dissolved in 15 ml of chloroform. The solution is cooled in an ice bath and a solution of 685 mg (0.0031 mole) of m-chloroperbenzoic acid (85%) in 10 ml of chloroform is added dropwise within 25 minutes. Stirring is continued for 30 minutes. The solution is washed successively with a 5% aqueous sodium hydrogen carbonate solution and water. It is then dried over magnesium sulfate and evaporated to dryness. A solid residue of 1.6 g of benzyl 6-(2''-phenylacetamido)-2',3',5',6'-tetrahydrospiro[penam-2,4'-[4H]thiopyran]-3-carboxylate 1'-oxyde is obtained. This product gives a single spot in thin layer chromatography on silica (eluent: benzene, ethyl acetate, acetic acid: 20:10:5 Rf = 0.45). Infra-red spectrum (CHCl$_3$) in cm$^{-1}$:

| | | |
|---|---|---|
| 3400 | NH | |
| 3000 | CH$_2$ | |
| 1785 | CO beta-lactam | |
| 1740 | CO ester | |
| 1680 | CO amide | |
| 1500 | phenyl | |
| 1040 | SO | |

N.M.R. (CDCl$_3$-TMS):

| ppm | multi-plicity | inte-gration | attribution |
|---|---|---|---|
| 1.4 to 3.4 | m | 8 H | twice: H$_{2'}$ H$_{3'}$ H$_{5'}$ and H$_{6'}$ |
| 3.65 | s | 2 H | CH$_2$ of phenylacetyl group |
| 4.6 | s | 1 H | H$_3$ |
| 5.2 | s | 2 H | CH$_2$ of benzyl group |
| 5.4 to 5.8 | m | 2 H | H$_5$ and H$_6$ |
| 6 to 6.5 | m | 1 H | NH |
| 7.4 | d | 10 H | two phenyl groups |

(d = doublet)
Mass spectrum: M$^+$· at m/e 498

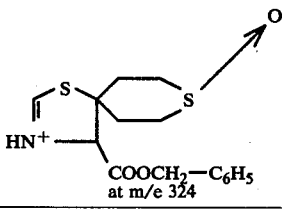

at m/e 324

I.2. Preparation of (2''-phenylacetamido)-spiro[oxa(or thia)cycloalkane-penam]carboxylic acids (a) 6-(2''-Phenylacetamido)-2',3',5',6'-tetrahydro-spiro[penam-2,4'-[4H]pyran]-3-carboxylic acid (potassium salt)

466 mg (0.001 mole) of benzyl 6-(2''-phenylacetamido)-2',3',5',6'-tetrahydrospiro[penam-2,4'-[4H]pyran]-3-carboxylate are dissolved in 50 ml of ethyl acetate. Hydrogenolysis is carried out under a pressure of 3 kg of hydrogen in the presence of 700 mg of Pd/C catalyst containing 10% of palladium. The catalyst is filtered off and rinsed with a little ethanol and then the filtrate is evaporated off to dryness. The residue is dissolved in 50 ml of dichloromethane, followed by the addition of 50 ml of water. The aqueous phase is brought to pH 7.2 with a dilute aqueous solution of potassium hydroxide, while stirring, and then decanted and finally lyophilized to give 370 mg (0.000788 mole; yield: 78.8% of theory) of potassium 6-(2''-phenylacetamido)-2',3',5',6'-tetrahydro-spiro[penam-2,4'-[4H]pyran]-3-carboxylate monohydrate. M.P. 218°–219° C.

Analysis for C$_{18}$H$_{20}$KN$_2$O$_5$S . H$_2$O (M.W. = 433) (as %)

| | | | |
|---|---|---|---|
| calculated : | C 50.0 | H 4.86 | N 6.48 |
| found : | 49.2 | 4.87 | 6.50 |

Infra-red spectrum (KBr) in cm$^{-1}$:

| | |
|---|---|
| 3460 | H$_2$O |
| 3250 | NH |
| 2940 | } CH and CH$_2$ |
| 2842 | |
| 1750 | CO beta-lactam |
| 1647 | CO amide |
| 1600 | CO of COOK group |
| 715 | } monosubstituted phenyl |
| 690 | |

(b) 6-(2''-Phenylacetamido)-2',3',5',6'-tetrahydro-spiro[penam-2,4'-[4H]thiopyran]-3-carboxylic acid (potassium salt)

This compound is prepared in the same manner as the preceding one. Yield: 50% of theory. M.P. 160°–167° C.

Analysis for C$_{18}$H$_{20}$KN$_2$O$_4$S$_2$ . 4H$_2$O (M.W. = 502) (as %)

| | | | |
|---|---|---|---|
| calculated : | C 43 | H 5.38 | N 5.58 |
| found : | 42.83 | 4.42 | 5.55 |

(c) The sodium salts corresponding to the potassium salts prepared hereinabove were prepared in the same way as the latter. The same method was used to prepare the sodium and potassium salts of the (2''-phenylacetamido)-spiro[oxa(or thia)cycloalkane-penam]-carboxylic acids from the corresponding benzyl esters described under 1(c) above.

(d) 6-(2''-Phenylacetamido)-2',3',5',6'-tetrahydro-spiro[penam-2,4'-[4H]thiopyran]-3-carboxylic acid 1'-oxide (potassium salt)

This compound is prepared in the same manner from the corresponding benzyl ester indicated in 1(d) above. M.P. 177°–203° C. (decomposition). Infra-red spectrum (KBr) in cm$^{-1}$:

| | |
|---|---|
| 1750 | CO beta-lactam |
| 1650 | CO amide |
| 1590 | CO of COOK group |

N.M.R. (D$_2$O-sodium dimethyl-2,2-sila-2-pentanesulfonate (DSS))

| ppm | multiplicity | integration | attribution |
|---|---|---|---|
| 1.5 to 3.4 | m | 8 H | twice: H$_{2'}$ H$_{3'}$ H$_{5'}$ and H$_{6'}$ |
| 3.65 | s | 2 H | CH$_2$ of phenylacetyl group |
| 4.35 | d | 1 H | H$_3$ |
| 5 to 5.8 | m | 2 H | H$_5$ and H$_6$ |
| 7.35 | s | 5 H | one phenyl group |

EXAMPLE II. Preparation of (2″-amino-2″-phenylacetamido)-spiro[oxa(or thia)cycloalkane-penam]-carboxylic acids and their derivatives

II.1. Preparation of benzyl (2″-amino-2″-phenylacetamido)-spiro[oxa(or thia)cycloalkane-penam]-carboxylates

(a) Benzyl 6-(2″-benzyloxycarbonylamino-2″-phenylacetamido)-2′,3′,5′,6′-tetrahydro-spiro[penam-2,4′-[4H]pyran]-3-carboxylate 1.56 g (0.003 mole) of benzyl 6-amino-2′,3′,5′,6′-tetrahydro-spiro[penam-2,4′-[4H]pyran]-3-carboxylate p-toluenesulfonate prepared as indicated in Example I.1.a) and 303 mg (0.003 mole) of triethylamine are mixed in 60 ml of dichloromethane. The light yellow solution obtained is cooled to between 0° and −5° C. 939 mg (0.0034 mole) of N-(benzyloxycarbonyl)-D(-)-2-phenylglycine and 678 mg of N,N′-dicyclohexylcarbodiimide are then added all at once. After stirring for 1 hour in the cold, the reaction mixture is left to return to ambient temperature overnight. After filtering off the N,N′-dicyclohexylurea formed, the organic phase in washed successively with dilute hydrochloric acid, with a 5% aqueous solution of sodium hydrogen carbonate and finally with water. After drying, it is evaporated to dryness to give 2.8 g of crude product. This product is purified by chromatography on a silica column (eluent: chloroform). In this way, there is obtained 1.6 g (yield 86.7% of theory) of benzyl 6-(2″-benzyloxycarbonylamino-2″-phenylacetamido)-2′,3′,5′,6′-tetrahydro-spiro[penam-2,4′-[4H]pyran]-3-carboxylate; M.P. 58°–59° C.

Analysis for $C_{33}H_{33}N_3O_7S$ (M.W. = 615) (as %)
calculated : C 64.39   H 5.37   N 6.83
found : 64.42   5.45   6.71
Infra-red spectrum (KBr) in $cm^{-1}$:
3310  NH
2945  ⎫
2850  ⎬ $CH_2$ and CH
1175  CO beta-lactam
1733  CO ester
1675  CO amide
1230  ester
745  ⎫
692  ⎬ monosubstituted phenyl

(b) Benzyl 6-(2″-benzyloxycarbonylamino-2″-phenylacetamido)-2′,3′,5′,6′-tetrahydro-spiro[penam-2,4′-[4H]thiopyran]-3-carboxylate This compound is obtained with a yield of 95% of theory, in the same manner as the preceding one, from benzyl 6-amino-2′,3′,5′,6′-tetrahydrospiro[penam-2,4′-[4H]thiopyran]-3-carboxylate p-toluenesulfonate (prepared as indicated in Example I.1(b)). M.P. 66°–69° C.

(c) Benzyl 6-(2″-benzyloxycarbonylamino-2″-phenylacetamido)-2′,3′,5′,6′-tetrahydro-spiro[penam-2,4′-[4H]thiopyran]-3-carboxylate 1′-oxide 2.5 g (0.0039 mole) of 6-(2″-benzyloxycarbonylamino-2″-phenylacetamido)-2′,3′,5′,6′-tetrahydro-spiro[penam-2,4′-[4H]thiopyran]-3-carboxylate (prepared as indicated in 1(b) hereinabove) are dissolved in 18 ml of chloroform. The solution is cooled in an ice bath and 757 mg (0.0037 mole) of m-chloroperbenzoic acid (85%) in 12 ml of chloroform are added thereto within 30 minutes. The solution is stirred for 30 minutes and then washed successively with a 5% aqueous sodium hydrogen carbonate solution and twice with water. After drying the organic phase and evaporating off the solvent, 2.6 g of benzyl 6-(2″-benzyloxycarbonylamino-2″-phenylacetamido)-2′,3′,5′,6′-tetrahydro-spiro[penam-2,4′-[4H]thiopyran]-3-carboxylate 1′-oxide are obtained.

This product gives a single spot in thin layer chromatography on silica:

| eluent | Rf |
| --- | --- |
| acetone | 0.8 |
| ethyl acetate | 0.5 to 0.6 |
| 98:2 chloroform/methanol | 0.4 |

Infra-red spectrum (KBr) in $cm^{-1}$:
3350  NH
3060  ⎫
     ⎬ $CH_2$ and CH
2900  
1775  CO beta-lactam
1720  CO ester
1675  CO amide
1490  NH amide
1040  SO
695   monosubstituted phenyl N.M.R. ($CDCl_3$-TMS):

| ppm | multiplicity | integration | attribution |
| --- | --- | --- | --- |
| 1.2 to 3.1 | m | 8 H | twice: $H_{2'}$ $H_{3'}$ $H_{5'}$ and $H_{6'}$ |
| 4.6 | s | 1 H | $H_3$ |
| 5.1 and 5.2 | 2 s | 4 H | two $CH_2$ of the benzyl groups |
| 5.2 to 5.7 | m | 3 H | $H_5$ $H_6$ and $H_{2''}$ |
| 7.1 to 7.7 | m | 15 H | three phenyl groups |

II.2. Preparation of (2″-amino-2″-phenylacetamido)-spiro[oxa(or thia)cycloalkane-penam]-carboxylic acids

(a) 6-(2″-Amino-2″-phenylacetamido)-2′,3′,5′,6′-tetrahydro-spiro[penam-2,4′-[4H]pyran]-3-carboxylic acid 1.5 g (0.0024 mole) of benzyl 6-(2″-benzyloxycarbonylamino-2″-phenylacetamido)-2′,3′,5′,6′-tetrahydro-spiro[penam-2,4′-[4H]pyran]-3-carboxylate are dissolved in 3 ml of ethyl acetate, followed by dilution with 300 ml of 96% ethanol. 5 g of Pd/C catalyst containing 10% of palladium are added and hydrogenolysis is carried out under a pressure of 3 kg of hydrogen for 30 minutes. After filtering off the catalyst and evaporating off the ethanol under reduced pressure at 30° to 35° C., the residue is taken up in water. This aqueous phase is extracted with ethyl acetate and then lyophilized to give 490 mg (0.0012 mole; yield: 50% of theory) of 6-(2″-amino-2″-phenylacetamido)-2′,3′,5′,6′-tetrahydro-spiro[penam-2,4′-[4H]pyran]-3-carboxylic acid; M.P. 188°–200° C.

Infra-red spectrum (KBr) in $cm^{-1}$:

3390  $NH_2$
2930  ⎫
     ⎬ $CH_2$
2880  
1764  CO beta-lactam
1680  CO amide
720   ⎫
690   ⎬ monosubstituted phenyl

N.M.R. (DMSO-TMS):

| ppm | multiplicity | integration | attribution |
| --- | --- | --- | --- |
| 1 to 2.2 | m | 4 H | two $H_{2'}$ and two $H_{6'}$ |

| | | | |
|---|---|---|---|
| 2.7 to 4.2 | m | 4 H | two H$_{3'}$ and two H$_{5'}$ |
| 4.5 | s | 1 H | H$_3$ |
| 5.1 to 5.6 | m | 2 H | H$_5$ and H$_6$ |
| 7.5 | s | 5 H | one phenyl group |

(b)
6-(2''-Amino-2''-phenylacetamido)-2',3',5',6'-tetrahydro-spiro[penam-2,4'-[4H]thiopyran]-carboxylic acid This compound is obtained in the same manner as the preceding one from benzyl 6-(2''-benzoyloxycarbonylamino-2''-phenylacetamido)-2',3',5',6'-tetrahydrospiro[penam-2,4'-[4H]thiopyran]-3-carboxylate. M.P. 188°–190° C.

Infra-red spectrum (KBr) in cm$^{-1}$:

| | |
|---|---|
| 3400 | NH$_2$ |
| 2900 | CH$_2$ |
| 1770 | CO beta-lactam |
| 1690 | CO amide |
| 695 | monosubstituted phenyl |

(c)
6-(2''-Amino-2''-phenylacetamido)-2',3',5',6'-tetrahydro-spiro[penam-2,4'-[4H]-thiopyran]-3-carboxylic acid 1'-oxide This compound is prepared with a 44% yield in the same manner as the two preceding ones from benzyl 6-(2''-benzyloxycarbonylamino-2''-phenylacetamido)-2',3',5',6'-tetrahydro-spiro[penam-2,4'-[4H]thiopyran]-3-carboxylate 1'-oxide (mentioned in 1(c) hereinabove). M.P. 190°–194° C.

Infra-red spectrum (KBr) in cm$^{-1}$:

| | |
|---|---|
| 3390 | NH$_2$ |
| 2920 | } CH$_2$ |
| 2820 | |
| 1770 | CO beta-lactam |
| 1675 | CO amide |
| 1500 | COO$^\ominus$ |
| 695 | monosubstituted phenyl |

(d) The following acids are prepared in the same manner:

6'-(2''-amino-2''-phenylacetamido)-4,5-dihydro-spiro[furan-3(2H),2'-penam]-3'-carboxylic acid;
6-(2''-amino-2''-phenylacetamido)-4',5'-dihydro-spiro[penam-2,3'(2'H)-thiophene]-3-carboxylic acid;
6'-(2''-amino-2''-phenylacetamido)-spiro[oxetane-3,2'-penam]-3'-carboxylic acid;
6-(2''-amino-2''-phenylacetamido)-spiro[penam-2,3'-thietane]-3-carboxylic acid.

EXAMPLE III. Preparation of (5''-methyl-3''-phenyl-4''-isoxazolecarboxamido)-spiro[oxa(or thia)cycloalkane-penam]-carboxylic acids and their derivatives (a)
6-(5''-Methyl-3''-phenyl-4''-isoxazolecarboxamido)-2',3',5',6'-tetrahydrospiro[penam-2,4'-[4H]pyran]-3-carboxylic acid (sodium salt).

2 ml of hexamethyldisilazane are added to a suspension of 840 mg (0.00325 mole) of 6-amino-2',3',5',6'-tetrahydro-spiro[penam-2,4'-[4H]pyran]-3-carboxylic acid (prepared by the method described in Example VI.1 of our Application Ser. No. 869,859 filed concurrently herewith) in 23 ml of anhydrous chloroform. The mixture is heated under reflux for 2 hours, dissolution being rapid. The solvent is distilled off in vacuo and the residue is taken up in 5 ml of chloroform and 5 ml of anhydrous dioxan. After cooling to 0° C., 325 mg (0.00325 mole) of triethylamine in 1 ml of chloroform are added. To this solution are added 720 mg (0.00325 mole) of 5-methyl-3-phenyl-4-isoxazolecarbonyl chloride in an anhydrous solvent mixture consisting of 3 ml of chloroform and 3 ml of dioxan, followed by stirring for 30 minutes to about 0° C. The reaction mixture is allowed to return to ambient temperature, a small amount of insoluble material is filtered off and 2 ml of ethanol are added. Stirring is continued for 20 minutes and then 414 mg (0.003 mole) of sodium 2-ethylbutyrate in 5 ml of isopropyl alcohol are added. The reaction mixture is allowed to stand for 2 hours and then 50 ml of anhydrous diethyl ether are added. There immediately appears a white precipitate which is filtered off. There are thus obtained 700 mg of sodium 6-(5''-methyl-3''-phenyl-4''-isoxazolecarboxamido)-2',3',5',6'-tetrahydrospiro[penam-2,4'-[4H]pyran]-3-carboxylate dihydrate (yield 47% of theory); M.P. 198°–203° C. (decomposition).

Analysis for $C_{21}H_{20}N_3NaO_6S \cdot 2H_2O$ (M.W. = 501) (as %)
| | | | |
|---|---|---|---|
| calculated : | C 50.29 | H 4.79 | N 8.38 |
| found : | 50.20 | 4.77 | 8.33 |

Infra-red spectrum (KBr) in cm$^{-1}$:

| | |
|---|---|
| 3400 | NH and H$_2$O |
| 2950 | CH$_2$ and CH$_3$ |
| 1760 | CO beta-lactam |
| 1645 | CO amide |
| 1595 | CO of COONa |
| 764 | } monosubstituted phenyl |
| 690 | |

N.M.R. (D$_2$O-DSS):

| ppm | multiplicity | integration | attribution |
|---|---|---|---|
| 1.2 to 2.5 | m | 4 H | two H$_{2'}$ and two H$_{6'}$ |
| 2.65 | s | 3 H | CH$_3$ at 5'' |
| 3.2 to 4.4 | m | 4 H | two H$_{3'}$ and two H$_{5'}$ |
| 4.33 | s | 1 H | H$_3$ |
| 5.65 | q (J=4 cps) | 2 H | H$_5$ and H$_6$ |
| 7.7 | s | 5 H | one phenyl group |

(b) In the same way, there are prepared the sodium salts of the following acids:

6-(5''-methyl-3''-phenyl-4''-isoxazolecarboxamido)-2',3',5',6'-tetrahydro-spiro[penam-2,4'-[4H]thiopyran]-3-carboxylic acid;
6'-(5''-methyl-3''-phenyl-4''-isoxazolecarboxamido)-4,5-dihydro-spiro[furan-3(2H),2'-penam]-3'-carboxylic acid;
6-(5''-methyl-3''-phenyl-4''-isoxazolecarboxamido)-4',5'-dihydro-spiro[penam-2,3'(2'H)-thiophene]-3-carboxylic acid;
6'-(5''-methyl-3''-phenyl-4''-isoxazolecarboxamido)-spiro[oxetane-3,2'-penam]-3'-carboxylic acid;
6-(5''-methyl-3''-phenyl-4''-isoxazolecarboxamido)-spiro[penam-2,3'-thietane]-3-carboxylic acid.

EXAMPLE IV. Preparation of (2'',6''-dimethoxybenzamido)-spiro[oxa(or thia)cycloalkane-penam]-carboxylic acids and their derivatives

IV.1. Benzyl 6-(2'',6''-dimethoxybenzamido)-2',3',5',6'-tetrahydro-spiro[penam-2,4'-[4H]thiopyran]-3-carboxylate 470 mg (0.0046 mole) of triethylamine in 4 ml of dichloromethane are added to a suspension of 2.5 g (0.0046 mole) of benzyl 6-amino-2',3',5',6'-tetrahydro-spiro[penam-2,4'-[4H]thiopyran]-3-carboxylate p-toluenesulfonate (prepared as indicated in Example I.1(b)) in 40 ml of dichloromethane. The product dissolves. A solution of 1.028 g (0.0051 mole) of 2,6-dimethoxybenzoyl chloride in 8 ml of dichloromethane and a solution of 518 mg (0.0051 mole) of triethylamine in 8 ml of dichloromethane are added successively thereto. The resulting solution is then successively washed with 0.05 N hydrochloric acid, with water, with an aqueous 5% sodium hydrogen carbonate solution and again with water. After drying and evaporating off the solvent, a residue of 2 g of benzyl 6-(2'',6''-dimethoxybenzamido)-2',3',5',6'-tetrahydro-spiro[penam-2,4'-[4H]thiopyran]-3-carboxylate is obtained. This compound is recrystalized from diethyl ether. M.P. 187°–190° C.

Analysis for $C_{26}H_{28}N_2O_6S_2$ (M.W. = 528) (as %)

| | C | H | N |
|---|---|---|---|
| calculated: | 59.0 | 5.30 | 5.30 |
| found: | 58.89 | 5.28 | 5.32 |

Infra-red spectrum (KBr) in $cm^{-1}$:

| | |
|---|---|
| 3380 | NH |
| 2850 | $CH_3$ |
| 1775 | CO beta-lactam |
| 1740 | CO ester |
| 1675 | CO amide |
| 1515 | NH amide |
| 695 | monosubstituted phenyl |

N.M.R. ($CDCl_3$-TMS):

| ppm | multi-plicity | inte-gration | attribution |
|---|---|---|---|
| 1.6 to 3.1 | m | 8 H | twice: $H_{2'}$ $H_{3'}$ $H_{5'}$ and $H_{6'}$ |
| 3.82 | s | 6 H | H of the two methoxy groups |
| 4.5 | s | 1 H | $H_3$ |
| 5.22 | s | 2 H | $CH_2$ of benzyl group |
| 5.5 to 6.1 | m | 2 H | $H_5$ and $H_6$ |
| 6.5 to 6.8 | m | 3 H | NH + $H_{3''}$ and $H_{5''}$ |
| 7.1 to 7.6 | m | 6 H | one phenyl group + $H_{4''}$ |

Mass spectrum = $M^{+\cdot}$ at m/e 528

$HN^+$ ... $COOCH_2$—$C_6H_5$ at m/e 308

IV.2(a) 6-(2'',6''-Dimethoxybenzamido)-2',3',5',6'-tetrahydro-spiro[penam-2,4'-[4H]thiopyran]-3-carboxylic acid (sodium salt)

This compound is obtained using the process described in Example I.2(a). M.P. 180°–200° C. (decomposition).

Infra-red spectrum (KBr) in $cm^{-1}$:

| | |
|---|---|
| 2830 | $CH_3$ |
| 1765 | CO beta-lactam |
| 1660 | CO amide |
| 1590 | $COO^{\ominus}$ |

N.M.R. ($D_2O$-DSS):

| ppm | multi-plicity | inte-gration | attribution |
|---|---|---|---|
| 1.8 to 3.2 | m | 8 H | twice: $H_{2'}$ $H_{3'}$ $H_{5'}$ and $H_{6'}$ |
| 3.85 | s | 6 H | H of the two methoxy groups |
| 4.28 | s | 1 H | $H_3$ |
| 4.7 to 5.62 | m | 2 H | $H_5$ and $H_6$ |
| 6.5 to 7.7 | m | 3 H | $H_{3''}$ $H_{4''}$ and $H_{5''}$ |

(b) The sodium salts of the following acids are prepared in the same manner:

6-(2'',6''-dimethoxybenzamido)-2',3',5',6'-tetrahydro-spiro[penam-2,4'-[4H]pyran]-3-carboxylic acid;

6'-2'',6''-dimethoxybenzamido)-4,5-dihydro-spiro[furan-3(2H),2'-penam]-3'-carboxylic acid;

6-(2'',6''-dimethoxybenzamido)-4',5'-dihydro-spiro[penam-2,3'(2'H)-thiophene]-3-carboxylic acid;

6'-(2'',6''-dimethoxybenzamido)-spiro[oxetane-3,2'-penam]-3'-carboxylic acid;

6-(2'',6''-dimethoxybenzamido)-spiro[penam-2,3'-thietane]-3-carboxylic acid.

Pharmacological properties

Numerous comparative tests have been carried out concerning the intrinsic biological activity of the compounds of general formula (I) according to the present invention towards various bacterial strains of the Gram-positive and Gram-negative type. The reference compounds for the comparative tests were penicillin G, oxacillin, ampicillin and methicillin. Information is given below regarding the origin and the characteristics of the bacterial strains employed:

A. Gram-positive bacterial strains

*Staphylococcus aureus* 6538

This is a Gram-positive coccus which is particularly sensitive to penicillins and which has a very low resistance mechanism. This strain of Staphylococcus is, therefore, representative of a maximum sensitivity of the species.

*Staphylococcus aureus* 52149

This is a Gram-positive coccus, the intrinsic sensitivity of the receptor of which is equivalent to that of the preceding strain but which produces a beta-lactamase which is typical of the species and which renders it resistant to all the penicillins which are sensitive to hydrolysis.

B. Gram-negative bacterial strains

*Escherichia coli* b

This is a well known collection strain of Escherichia coli which produces very little beta-lactamase (of type I) and is, therefore, very sensitive to penicillins. As regards the classification of the beta-lactamases, use is here made of that proposed by M. H. RICHMOND and R. B. SYKES (see Advances in Microbial Physiology, 9, (1973), 43 and 45).

*Eschericha coli* B AMPI-R

This is a mutant of the preceding strain, which we have produced. This strain is, on the contrary, a hyper-producer of beta-lactamase of type I, already produced by the parent strain Escherichia coli B. It has an increased resistance to penicillins, which would appear to be directly connected with the production of beta-lactamase.

*Escherichia coli* K 12-44

This is a mutant of Escherichia coli K 12, the reference parent strain typical of the species. This mutant is not a producer of beta-lactamase.

*Escherichia coli* K 12-44 S

This is a pleiotropic mutant of Escherichia coli K 12-44, which does not produce beta-lactamase and which we have produced. It is very sensitive to penicillins due to hyperpermeability.

*Escherichia coli* K 12-44 R

This strain is a pleiotropic mutant of Escherichia coli K 12-44, which we have produced. It is not a producer of beta-lactamase but, nevertheless, it has a resistance to penicillins, probably as a result of the modification of the permeability of the cell membranes.

C. Results of the comparative tests of activity

For a certain number of compounds of general formula (I) according to the present invention, a determination was carried out of the minimum inhibitory concentration (abbreviated MIC) according to the procedure described below.

The products to be tested are introduced in increasing concentrations into a gelose culture medium in Petri dishes. A multiple inoculator is used to deposit simultaneously drops (10 microliters) of inoculum (suspension of about $10^5$ bacteria per ml) onto the surface of the medium. After incubation at 37° C. for 24 hours, the growth of the bacteria is observed. By definition, the MIC is expressed as the minimum concentration of the tested compounds which inhibits the multiplication of the bacteria. In the results which follow, however, the MIC is given as being equal to 1 for the reference compounds and the activity figures given for the tested compounds of general formula (I) are, therefore, relative values. This presentation of the results is more correct and the most reproducible, because, for one and the same bacterial strain, different MIC values can be observed if they are measured at different times. This is bound up with the "seasonal" variations in the strains and their nutrient medium.

The compounds which were tested are as follows:

Compound A: 6-(2''-phenylacetamido)-2',3',5',6'-tetrahydro-spiro[penam-2,4'-[4H]pyran]-3-carboxylic acid (potassium salt) (formula I: n=m=2, X=O, $R_1$=H, $R_2$=2-phenylacetyl).

Compound B: 6-(2''-amino-2''-phenylacetamido)-2',3',5',6'-tetrahydro-spiro[penam-2,4'-[4H]pyran]-3-carboxylic acid. (formula I: n=m=2, X=O, $R_1$=H, $R_2$=2-amino-2-phenylacetyl);

Compound C: 6C-(5''-methyl-3''-phenyl-4''-isoxazolecarboxamido)-2',3',5',6'-tetrahydro-spiro[penam-2,4'-[4H]pyran]-3-carboxylic acid (sodium salt) (formula I: n=m=2, X=O, $R_1$=H, $R_2$=5-methyl-3-phenyl-4-isoxazolecarbonyl);

Compound E: 6-(2''-phenylacetamido)-2',3',5',6'-tetrahydro-spiro[penam-2,4'-[4H]thiopyran]-3-carboxylic acid (potassium salt) (formula I: n=m=2, X=S, $R_1$=H, $R_2$=2-phenylacetyl);

Compound F: 6-(2''-amino-2''-phenylacetamido)-2',3',5',6'-tetrahydro-spiro[penam-2,4'-[4H]thiopyran]-3-carboxylic acid (formula I: n=m=2, X=S, $R_1$=H, $R_2$=2-amino-2-phenylacetyl);

Compound G: 6-(2'',6''-dimethoxybenzamido)-2',3',5',6'-tetrahydro-spiro[penam-2,4'-[4H]thiopyran]-3-carboxylic acid (sodium salt) (formula I: n=m=2, X=S, $R_1$=H, $R_2$=2,6-dimethoxybenzoyle);

Compound H: 6-(2''-phenylacetamido)-2',3',5',6'-tetrahydro-spiro[penam-2,4'-[4H]thiopyran]-3-carboxylic acid 1'-oxide (potassium salt) (formula I: n=m=2, X=SO, $R_1$=H, $R_2$=2-phenylacetyl);

Compound J: 6-(2''-amino-2''-phenylacetamido)-2',3',5',6'-tetrahydro-spiro[penam-2,4'-[4H]thiopyran]-3-carboxylic acid 1'-oxide (formula I: n=m=2, X=SO, $R_1$=H, $R_2$=2-amino-2-phenylacetyl).

| a) Comparative tests with penicillin G. | | | | |
|---|---|---|---|---|
| Strain used | Penicillin G | Compound A | Compound E | Compound H |
| S.AUREUS 6538 | 1 | 2 | 10 | 1 |
| S.AUREUS 52149 | 1 | 2 | 1 | 1 |
| E.COLI B | 1 | 4 | 5 | 1 |
| E.COLI B AMPI-R | 1 | 2 | >2 | — |
| b) Comparative tests with oxacillin. | | | | |
| Strain used | Oxacillin | Compound | | |
| S.AUREUS 6538 | 1 | 2 | | |
| S.AUREUS 52149 | 1 | 1 | | |
| c) Comparative tests with ampicillin. | | | | |
| Strain used | Ampicillin | Compound B | Compound F | Compound J |
| S.AUREUS 6538 | 1 | 1 | 2 | 2 |
| E.COLI B | 1 | 3.5 | 7 | 1 |
| E.COLI B AMPI-R | 1 | 1 | 3 | 2 |
| E.COLI K 12-44 | 1 | 3.5 | 10 | 3 |
| E.COLI K 12-44S | 1 | 1.9 | 15 | 3 |
| E.COLI K 12-44R | 1 | 1.5 | >1.5 | 2 |
| d) Comparative test with methicillin. | | | | |
| Strain used | Methicillin | Compound G | | |
| S.AUREUS 52149 | 1 | 0.5 | | |

It can be seen from these results that the compounds of general formula (I) according to the present invention have activities which are comparable with those of the corresponding known penicillins. However, the essential interest of these new compounds comes forth from the following: the compounds of general formula (I) differ from the known penicillins by an increased resistance to beta-lactamases, which are the deactivating enzymes hydrolyzing the lactam function of the penicillanic ring.

This property of the compounds of the present invention is demonstrated by the results of the comparison of the hydrolysis kinetics of compound B with that of ampicillin, in the presence of two beta-lactamases of Gram-negative bacteria. These results are set out in the following Table:

| Residual activities (in micromoles) of ampicillin and Compound B in the presence of beta-lactamases, as a function of time | | | | | |
|---|---|---|---|---|---|
| beta-lactamase TEM | | | beta-lactamase P 99 | | |
| Incubation time (minutes) | Ampicillin | Compound B | Incubation time (minutes) | Ampicillin | Compound B |
| 0 | 500 | 500 | 0 | 500 | 500 |
| 2 |  | 469 | 3 | 262 | 458 |
| 4 |  | 453 | 6 | 138 | 422 |
| 6 | <50 | 438 | 9 | <50 | 334 |
| 12 | <50 | 334 | 12 | <50 | 312 |
| 18 | <50 | 225 | 20 | <50 | 300 |

These results show that, after incubation for 6 minutes in beta-lactamase TEM, the activity of ampicillin is no more detectable, whilst there still remains an activity of compound B corresponding to 438 micromoles, i.e. 87%. The same observation was made in the case of beta-lactamase P 99: after incubation for 9 minutes, the activity of ampicillin is no more detectable, whereas there still remains an activity of compound B corresponding to 334 micromoles, i.e. 67%.

These results are also confirmed by the activity tests which have been described above. Indeed, it can be seen that between the activity of compound B on E. COLI B and on its mutant, which is a hyperproducer of beta-lactamase, E. COLI B Ampi-R, there is a difference of a factor of 3.5.

An increased resistance to these beta-lactamases also has been found for compound F. This is however less pronounced than in the case of compound B. No change in behavior towards these beta-lactamases has been detected for compound J, as compared with ampicillin.

A very pronounced increase in resistance to beta-lactamase TEM has also been found for compounds E and H, which are homologues of penicillin G. This property can be shown by measuring the rate of hydrolysis expressed in terms of the number of microliters of sodium hydroxide of a given concentration which are consumed per minute. This method allows the dosage of the penicilloic acid resulting from the hydrolysis of the beta-lactam function by the lytic enzyme. The results of these kinetics, as given in the following Table, clearly show the superiority of compounds E and H as compared with penicillin G.

| Compound | microliters 0.005 N NaOH consumed per minute |
|---|---|
| Penicillin G | 3.83 |
| Compound E | 0.64 |
| Compound H | 0.50 |

This confirms the importance of the compounds of formula (I) as compared with the known penicillins, particularly for combating the Gram-negative strains which produce beta-lactamases.

D. Posology and use

The compounds of formula (I), as all penicillins, can be administered orally or parenterally.

For example, the posology of compound A is between 0.4 and 6 g per day, that of compound C between 4 and 8 g per day, that of compound E between 2 and 10 g per day and that of compound H between 0.2 and 3 g per day. For the homologues of ampicillin (compounds B, F and J), an identical posology of 0.7 to 7 g per day can be adopted; these doses can of course be adapted in function of the patient and the disease to be treated.

We claim:

1. An amino-spiro[oxa(or thia) cycloalkane-penam]-carboxylic acid derivative compound of the formula $$\begin{array}{c} R_1 \\ \diagdown \\ R_2 \diagup N-CH-CH \diagup S \diagdown (CH_2)_n \diagdown \\ | \quad | \quad C \quad \diagdown X \\ R_2 \diagup C-N-CH(CH_2)_m \diagup \\ O \quad \quad COOH \end{array}$$

wherein X is a sulfur or oxygen atom or a sulfinyl group,
n is 1 or 2,
m is 1 or 2,
$R_1$ is a hydrogen atom and
$R_2$ is a radical selected from the group consisting of 2-phenyl-acetyl, 2-amino-2-phenylacetyl, 5-methyl-3-phenyl-4-isoxazole-carbonyl and 2,6-dimethoxybenzoyl, or
$R_1$ and $R_2$ together represent (hexahydro-1H-azepin-1-yl) methylene, and a therapeutically acceptable non-toxic salt thereof.

2. A compound as claimed in claim 1, wherein $R_2$ is a radical selected from the group consisting of 2-phenylacetyl, 2-amino-2-phenylacetyl, 5-methyl-3-phenyl-4-isoxazolecarbonyl and 2,6-dimethoxybenzoyl.

3. A compound as claimed in claim 1, wherein $R_1$ and $R_2$ together represent (hexahydro1H-azepin-1-yl)methylene.

4. A compound as claimed in claim 1, namely potassium 6-(2″-phenylacetamido)-2′,3′,5′,6′-tetrahydro-spiro[penam-2,4′-[4H]pyran]-3-carboxylate.

5. A compound as claimed in claim 1, namely potassium 6-(2″-phenylacetamido)-2′,3′,5′,6′-tetrahydro-spiro[penam-2,4′-[4H]thiopyran]-3-carboxylate.

6. A compound as claimed in claim 1, namely potassium 6-(2″-phenylacetamido)-2′,3′,5′,6′-tetrahydro-spiro[penam-2,4′-[4H]thiopyran]-3-carboxylate 1′-oxide.

7. A compound as claimed in claim 1, namely 6-(2″-amino-2″-phenylacetamido)-2′,3′,5′,6′-tetrahydro-spiro[penam-2,4′-[4H]pyran]-3-carboxylic acid.

8. A compound as claimed in claim 1, namely 6-(2″-amino-2″-phenylacetamido)-2′,3′,5′,6′-tetrahydro-spiro[penam-2,4′-[4H]thiopyran]-3-carboxylic acid.

9. A compound as claimed in claim 1, namely 6-(2″-amino-2″-phenylacetamido)-2′,3′,5′,6′-tetrahydro-spiro[penam-2,4′-[4H]thiopyran]-3-carboxylic acid 1′-oxide.

10. A compound as claimed in claim 1, namely sodium 6-(5″-methyl-3″-phenyl-4″-isoxazolecarboxamido)-2′,3′,5′,6′-tetrahydro-spiro[penam-2,4′-[4H]pyran]-3-carboxylate.

11. A compound as claimed in claim 1, namely sodium 6-(2″,6″-dimethoxybenzamido)-2′,3′,5′,6′-tetrahydro-spiro[penam-2,4′-[4H]thiopyran]-3-carboxylate.

12. A composition for the treatment of an infectious disease caused by Gram-positive or Gram-negative bacteria, which comprises a pharmaceutical carrier and a therapeutically effective amount of an amino-spiro[oxa(or thia) cycloalkanepenam]-carboxylic acid derivative compound of the formula

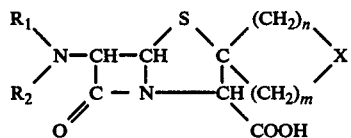

wherein X is a sulfur or oxygen atom or a sulfinyl group,
n is 1 or 2,
m is 1 or 2,
$R_1$ is a hydrogen atom and $R_2$ is a radical selected from the group consisting of 2-phenylacetyl, 2-amino-2-phenylacetyl, 5-methyl-3-phenyl-4-isoxazolecarbonyl and 2,6-dimethoxybenzoyl, or
$R_1$ and $R_2$ together represent (hexahydro-1H-azepin-1-yl)methylene, and a therapeutically acceptable non-toxic salt thereof.

13. A method of treating infectious diseases caused by Gram-positive and Gram-negative bacteria in warm-blooded animals which comprises administering to said animals a therapeutically effective amount of an amino-spiro[oxa(or thia) cycloalkane-penam]carboxylic acid derivative compound of the formula

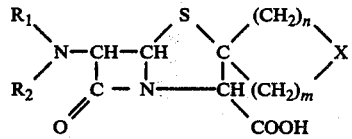

wherein X is a sulfur or oxygen atom or a sulfinyl group,
n is 1 or 2,
m is 1 or 2,
$R_1$ is a hydrogen atom and $R_2$ is a radical selected from the group consisting of 2-phenylacetyl, 2-amino-2-phenylacetyl, 5-methyl-3-phenyl-4-isoxazolecarbonyl and 2,6-dimethoxybenzoyl, or
$R_1$ and $R_2$ together represent (hexahydro-1H-azepin-1-yl)methylene, and a therapeutically acceptable non-toxic salt thereof.

* * * * *